(12) United States Patent
Litvak et al.

(10) Patent No.: US 8,126,565 B1
(45) Date of Patent: *Feb. 28, 2012

(54) SOUND PROCESSING AND STIMULATION SYSTEMS AND METHODS FOR USE WITH COCHLEAR IMPLANT DEVICES

(75) Inventors: Leonid M. Litvak, Los Angeles, CA (US); Lakshmi N. Mishra, Valencia, CA (US); Gene Y. Fridman, Santa Clarita, CA (US); Lee F. Hartley, Calgary (CA)

(73) Assignee: Advanced Bionics, Valencia, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 12/418,428

(22) Filed: Apr. 3, 2009

Related U.S. Application Data

(63) Continuation of application No. 11/080,214, filed on Mar. 14, 2005, now Pat. No. 7,515,966.

(51) Int. Cl.
*A61N 1/00* (2006.01)
(52) U.S. Cl. .......................................................... 607/57
(58) Field of Classification Search ...................... 607/57
See application file for complete search history.

(56) References Cited

U.S. PATENT DOCUMENTS

| 4,400,590 | A | 8/1983 | Michelson |
| 4,532,930 | A | 8/1985 | Crosby et al. |
| 4,592,359 | A | 6/1986 | Galbraith |
| 4,947,844 | A | 8/1990 | McDermott |
| 5,029,217 | A | 7/1991 | Chabries et al. |
| 5,597,380 | A | 1/1997 | McDermott et al. |
| 5,603,726 | A | 2/1997 | Schulman et al. |
| 5,626,629 | A | 5/1997 | Faltys et al. |
| 5,824,022 | A | 10/1998 | Zilberman et al. |
| 5,895,416 | A | 4/1999 | Barreras et al. |
| 6,129,753 | A | 10/2000 | Kuzma |
| 6,181,969 | B1 | 1/2001 | Gord |
| 6,219,580 | B1 | 4/2001 | Faltys et al. |

(Continued)

FOREIGN PATENT DOCUMENTS

WO WO-2004043537 5/2004

OTHER PUBLICATIONS

Final Office Action received in U.S. Appl. No. 12/418,471 dated Feb. 15, 2011.

(Continued)

*Primary Examiner* — George Manuel
(74) *Attorney, Agent, or Firm* — AdvantEdge Law Group, LLC

(57) ABSTRACT

Sound processing strategies for use with cochlear implant systems utilizing simultaneous stimulation of electrodes are provided. The strategies include computing a frequency spectrum of a signal representative of sound, arranging the spectrum into channels and assigning a subset of electrodes to each channel. Each subset is stimulated so as to stimulate a virtual electrode positioned at a location on the cochlea that corresponds to the frequency at which a spectral peak is located within an assigned channel. The strategies also derive a carrier for a channel having a frequency that may relate to the stimulation frequency so that temporal information is presented. In order to fit these strategies, a group of electrodes is selected and the portion of the current that would otherwise be applied to electrode(s) having a partner electrode in the group is applied to the partner electrode.

19 Claims, 11 Drawing Sheets

U.S. PATENT DOCUMENTS

| | | | |
|---|---|---|---|
| 6,249,704 B1 | 6/2001 | Maltan et al. | |
| 6,272,382 B1 | 8/2001 | Faltys et al. | |
| 6,289,247 B1 | 9/2001 | Faltys et al. | |
| 6,308,101 B1 | 10/2001 | Faltys et al. | |
| 6,415,186 B1 * | 7/2002 | Chim et al. | 607/57 |
| 6,480,820 B1 | 11/2002 | Clopton et al. | |
| 6,505,078 B1 | 1/2003 | King et al. | |
| 6,988,006 B2 | 1/2006 | King et al. | |
| 7,039,466 B1 | 5/2006 | Harrison et al. | |
| 7,107,101 B1 | 9/2006 | Faltys | |
| 7,149,583 B1 | 12/2006 | Litvak | |
| 7,515,966 B1 | 4/2009 | Litvak et al. | |
| 2004/0002852 A1 | 1/2004 | Kim | |
| 2004/0136556 A1 | 7/2004 | Litvak et al. | |

OTHER PUBLICATIONS

O. Poroy et al., "Pitch Perception Using Virtual Channels", Conference on Implantable Auditory Prostheses, Asilomar, Monterey, CA, 2001 (printed Sep. 19, 2005 at http://www.utdallas.edu/-loizou/cimplants/virtual.pdf).

Advanced Bionics Corporation, "New Methodology for Fitting Cochlear Implants", Marketing White Paper, Jun. 2003 (printed Sep. 19, 2005 at http://www.bionicear.com/printables/NewMethodology.pdf).

Schatzer et al., "Eleventh Quarterly Progress Report for NIH Project N01-DC-2-1002 (Oct. 1 through Dec. 31, 2004)—Speech Processors for Auditory Prostheses", Research Triangle Institute, 2005.

Lawson et al., "Tenth Quarterly Progress Report for NIH Project N01-DC-2-1002 (Jul. 1 through Sep. 30, 2004)—Speech Processors for Auditory Prostheses", Research Triangle Institute, 2004.

Cartee et al., "Ninth Quarterly Progress Report for NIH Project N01-DC-2-1002 (Apr. 1 through Jun. 30, 2004)—Speech Processors for Auditory Prostheses", Research Triangle Institute, 2004.

Wilson et al., "Eighth Quarterly Progress Report for NIH Project N01-DC-2-1002 (Jan. 1 through Mar. 31, 2004)—Speech Processors for Auditory Prostheses", Research Triangle Institute, 2004.

Wilson et al., "Seventh Quarterly Progress Report for NIH Project N01-DC-2-1002 (Oct. 1 through Dec. 31, 2003)—Speech Processors for Auditory Prostheses", Research Triangle Institute, 2004.

Schatzer et al., "Sixth Quarterly Progress Report for NIH Project N01-DC-2-1002 (Jul. 1 through Sep. 30, 2003)—Speech Processors for Auditory Prostheses", Research Triangle Institute, 2003.

Schatzer et al., "Fifth Quarterly Progress Report for NIH Project N01-DC-2-1002 (Apr. 1 through Jun. 30, 2003)—Speech Processors for Auditory Prostheses", Research Triangle Institute, 2003.

Wolford et al., "Fourth Quarterly Progress Report for NIH Project N01-DC-2-1002 (Jan. 1 through Mar. 31, 2003)—Speech Processors for Auditory Prostheses", Research Triangle Institute, 2003.

Wilson et al., "Third Quarterly Progress Report for NIH Project N01-DC-2-1002 (Oct. 1 through Dec. 31, 2002)—Speech Processors for Auditory Prostheses", Research Triangle Institute, 2003.

Lawson et al., "Second Quarterly Progress Report for NIH Project N01-DC-2-1002 (Jul. 1 through Sep. 30, 2002)—Speech Processors for Auditory Prostheses", Research Triangle Institute, 2002.

Lawson et al., "First Quarterly Progress Report for NIH Project N01-DC-2-1002 (Apr. 1 through Jun. 30, 2002) Speech Processors for Auditory Prostheses", Research Triangle Institute, 2002.

Wilson et al., "Final Report for NIH Project N01-DC-82105 (Sep. 30, 1998 through Mar. 30, 2002) Speech Processors for Auditory Prostheses", Research Triangle Institute, 2002.

Wilson et al., "Final Report for NIH Project N01-DC-22401 (Aug. 1, 1992 through Jul. 31, 1995)—Speech Processors for Auditory Prostheses", Research Triangle Institute, 1995.

Wilson et al., "Sixth Quarterly Progress Report for NIH Project N01-DC-2-2401 (Nov. 1, 1993 through Jan. 31, 1994)—Speech Processors for Auditory Prostheses", Research Triangle Institute, 1994.

Wilson et al., "Third Quarterly Progress Report for NIH Project N01-DC-2-2401 (Feb. 1 through Apr. 30, 1993)—Speech Processors for Auditory Prostheses", Research Triangle Institute, 1993.

Wilson et al., "First Quarterly Progress Report for NIH Project N01-DC-2-2401 (Aug. 1 through Oct. 31, 1992)—Speech Processors for Auditory Prostheses", Research Triangle Institute, 1992.

Non-Final Office Action received in U.S. Appl. No. 12/418,471 dated Nov. 5, 2010.

* cited by examiner

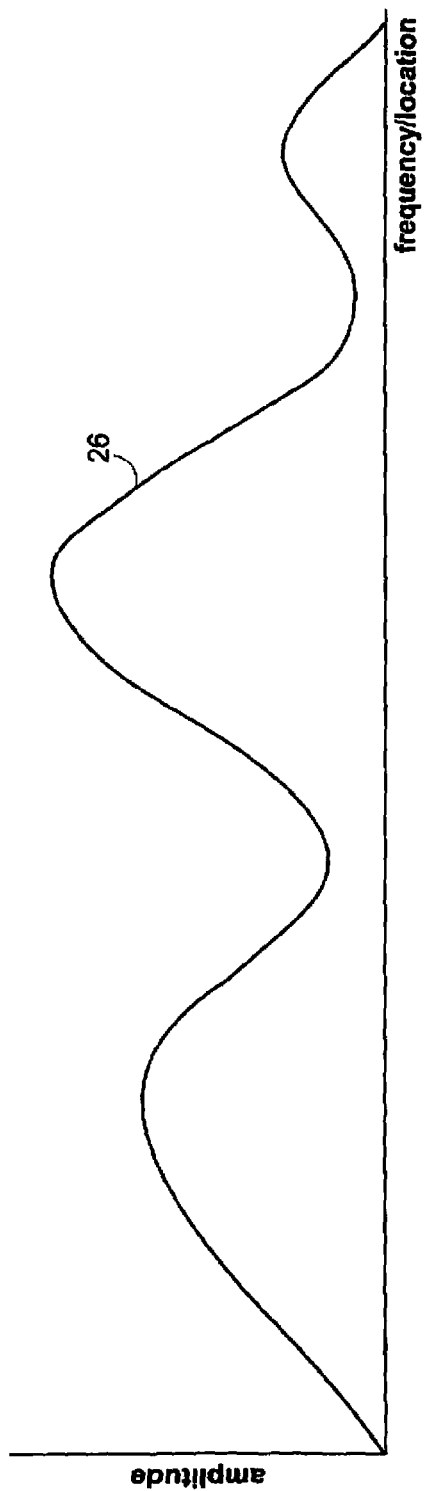
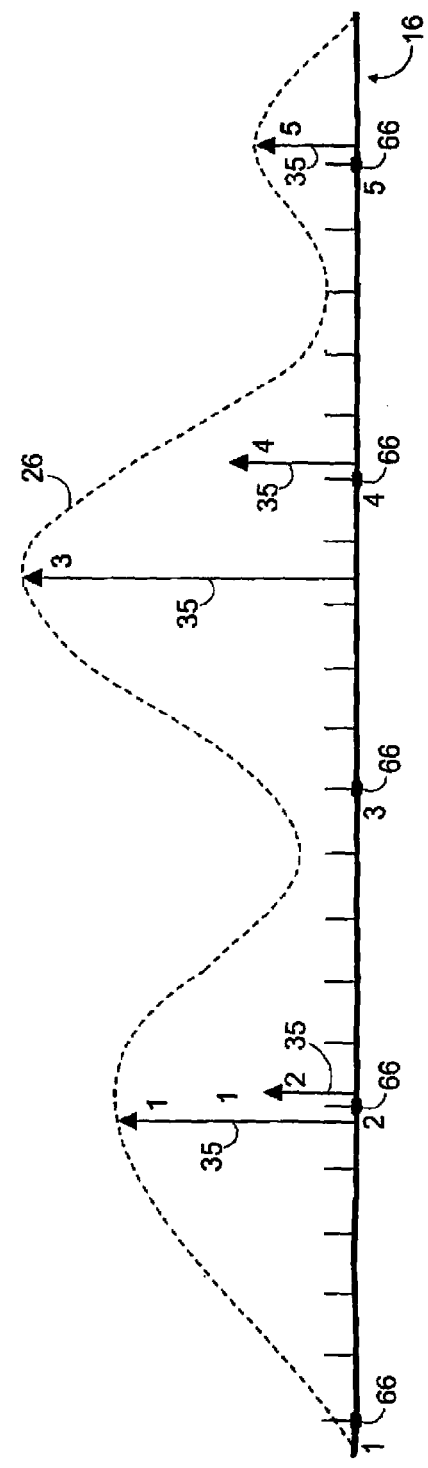
FIG. 2
FIG. 3

SOUND PROCESSING AND STIMULATION SYSTEMS AND METHODS FOR USE WITH COCHLEAR IMPLANT DEVICES

RELATED APPLICATIONS

The present application is a continuation application of U.S. patent application Ser. No. 11/080,214, filed Mar. 14, 2005, which application is incorporated herein by reference in its entirety.

BACKGROUND

Hearing loss, which may be due to many different causes, is generally of two types: conductive and sensorineural. Conductive hearing loss occurs when the normal mechanical pathways for sound to reach the hair cells in the cochlea are impeded. Conductive hearing loss may often be helped by use of conventional hearing aids, which amplify sound so that acoustic information reaches the cochlea and the hair cells. Sensorineural hearing loss, on the other hand, is usually due to the absence or impairment of the hair cells which are needed to transduce acoustic signals in the cochlea into nerve impulses that are sent to the auditory nerve. People suffering from severe sensorineural hearing loss are usually unable to derive any benefit from conventional hearing aid systems because their mechanisms for transducing sound energy into auditory nerve impulses are non-existent or have been severely damaged.

Cochlear implant technology seeks to overcome sensorineural hearing loss by bypassing the hair cells in the cochlea and presenting electrical stimulation to the auditory nerve directly, leading to the perception of sound in the brain and at least partial restoration of hearing. Indeed, cochlear implant technology may be used to bypass the outer, middle and inner ears. Cochlear implant systems that utilize such technology have been successfully used to restore hearing in sensorineural deaf patients.

Generally, a cochlear implant system includes an external portion and an implanted portion that are separated by a skin barrier. The external portion usually includes a power source, a microphone and a signal processing device, whereas the implanted portion usually includes a stimulation device and an electrode array. The power source supplies power to the system. Sound enters the system through the microphone which delivers it to the signal processing device as an electrical signal. The signal processing device processes the signal and transmits it to the stimulation device through the skin barrier. The stimulation device uses the received signal to stimulate electrodes in the electrode array that is implanted into the cochlea. The electrodes in the array transmit electrical stimuli to the nerve cells that emanate from the cochlea and that are part of the auditory nerve. These nerve cells are arranged in an orderly tonotopic sequence, from high frequencies near the initial (basal) end of the cochlear coil to progressively lower frequencies towards the inner end of the coil (apex). Nerve cells emanating from the various regions of the cochlea are associated with the frequencies that most efficiently stimulate those regions, and the brain, which receives neural impulses from the auditory nerve, maps those frequencies in accord with this association.

Conventional cochlear implants separate sound signals into a number of parallel channels of information, each representing the intensity of a narrow band of frequencies within the acoustic spectrum. Ideally, each channel of information would be conveyed selectively to the subset of nerve cells located along the cochlea that would have normally transmitted information about that frequency band to the brain. This would require placing the electrode array along the entire length of the cochlear ducts, which is surgically impractical. Instead, the electrode array is typically inserted into the scala tympani, one of the three parallel ducts that make up the spiral shape of the cochlea. The array of linearly arranged electrodes is inserted such that the electrode closest to the basal end of the coil is associated with the highest frequency band and the electrode closest to apex is associated with the lowest frequency band. Each location along the implanted length of the cochlea may be mapped to a corresponding frequency, thereby yielding a frequency-to-location table for the electrode array. The foregoing illustrates the relationship between frequency and physical location in the cochlea—i.e., the cochlear frequency/location correspondence.

The performance of a cochlear implant system is limited mainly by the amount of information that can be delivered by electrical stimulation to the patient, which, in turn, is limited by the number of electrodes in the implant. The number of electrodes that can be used is limited by the size of the scala tympani and the distance or spatial separation between electrodes. While the size of the scala tympani presents an anatomical limitation, it is possible to reduce the distance between electrodes. However, reducing such spatial separation increases electrode interaction and interference, which could have undesirable effects. It is however possible to use such effects to deliver additional spectral information in a suitable manner.

Recent studies have shown that simultaneously stimulating two adjacent electrodes in such systems results in patients perceiving a pitch that is between the two pitches perceived when each electrode is stimulated individually. Moreover, as the stimulation current is changed from being entirely applied to the first electrode to the second electrode, pitch sensation changes from the pitch associated with the first electrode to the pitch associated with the second electrode in a continuous fashion. This is because the electric field resulting from stimulating one of the electrodes is likely to be superposed to that resulting from stimulating the other electrode. The superposed electric fields are centered around a virtual electrode that lies between the two adjacent electrodes. Furthermore, the perceived loudness stays roughly constant so long as the sum of the currents applied to the electrode pair stays roughly constant. Thus, it is possible to stimulate a virtual electrode located between adjacent electrodes by simultaneously stimulating these electrodes using relative current weights, whereby the frequency band associated with the virtual electrode corresponds to one that lies between the frequency bands associated with the individual electrodes.

The challenge lies in utilizing a sound processing strategy that makes use of such virtual electrodes. Although separate channels could be assigned to individual electrodes and virtual electrodes, such a processing scheme limits the number of virtual electrodes that may be stimulated unless the number of channels is significantly increased. Increasing the number of channels, however, demands additional processing capabilities which may result in delays or may require more power and more complicated circuitry.

Frequencies that may be associated with optimal virtual electrodes may instead be estimated. One example of a known system that estimates frequencies using conventional methods, such as calculating the instantaneous frequency along with phase angle and magnitude values, is described in U.S. Pat. No. 6,480,820. However, such methods result in inconsistent representations of spectral sound information. This is because adding sound components to the sound stimulus may result in a drastic and disproportional shift in the location on the electrode array to be stimulated. Thus, there is a need for improved frequency computation for presentation of spectral information in sound processing strategies that can be used with cochlear implant systems that utilize simultaneous stimulation of several electrodes.

When a cochlear implant is provided to a patient, it is necessary to initially fit the system in order for it to better perform its intended function of helping a patient to sense sound at appropriate levels. A common method of fitting involves presenting a known sound stimulus to a patient while a subset of the electrode array is activated and adjusting the level of corresponding electrical current applied to the array such that the sound perceived by the patient is of appropriate loudness. In applying such a method, it is assumed that the perceived loudness will not be affected by the activity of adjacent electrodes once the full array is activated, including electrodes that were previously deactivated. However, when adjacent electrodes are stimulated simultaneously, the resulting electric fields are likely to be superposed thereby affecting the loudness perceived by the patient, as mentioned above. Thus, there is a need for fitting sound processing strategies used with cochlear implant systems that utilize simultaneous stimulation of several electrodes.

In addition to accounting for spectral information and loudness, a cochlear implant system should preserve, as much as possible, temporal information that is key to differentiate various sounds. Presenting fine temporal information is critical for the perception of overall sound quality, clarity, speech and music. There is therefore also a need for improved time detection for presentation of temporal information in sound processing strategies used with the cochlear implant systems described above.

SUMMARY

The present invention addresses the above and other needs by providing systems and methods that can be used with cochlear implant devices that utilize simultaneous stimulation of several electrodes. A cochlear implant system having sound processing circuitry coupled to an electrode array may be provided. The sound processing circuitry may be adapted to compute a frequency spectrum of a signal representative of sound and arrange the frequency spectrum into a plurality of channels such that each channel corresponds to a range of frequencies that lie within the frequency spectrum. For example, FFT circuitry may perform a Discrete Fourier Transform on the signal in order to compute its frequency spectrum.

The electrode array may be inserted into the cochlea such that a subset of electrodes is associated with at least one of the plurality of channels. A stream of pulse sets may be simultaneously applied to the electrodes in the subset so as to stimulate a virtual electrode positioned at a location on the cochlea that corresponds to a stimulation frequency computed for a particular channel. An improved computation of the stimulation frequency may be calculated or estimated using the sound processing circuitry as the frequency at which a spectral peak is located within the range of frequencies that corresponds to the channel. For example, such a computation may be implemented using a peak locator through energy computation and function fitting or estimation. Different subsets of electrodes may be associated with the plurality of channels such that the electrode array may be used to stimulate the auditory nerve at computed stimulation frequencies that range over the computed spectrum.

The stream of pulse sets applied to each subset of electrodes may be derived from a current that may be modified based partly on an envelope computed by the sound processing circuitry. To do so, the processing circuitry may divide at least one of the channels into a plurality of sub-channels having smaller ranges of frequencies and compute a square root of a sum of the squared Hilbert envelopes for each of the plurality of sub-channels. Such a process may be applied to, for example, the channel assigned to the largest bandwidth in the computed spectrum.

A method for fitting such a sound processing strategy that utilizes simultaneous stimulation of a subset of electrodes may be described in the following. A fitting group that includes at least one electrode may be selected and all other electrodes may be disabled. The portion of the current that would otherwise be applied to an electrode that is not part of the fitting group and that has a partner electrode in the fitting group is applied instead to the partner electrode in the fitting group. A partner electrode may be one associated with an electric field that is superposed to that of the electrode that is not part of the fitting group so as to stimulate a virtual electrode positioned at a location that lies between the location of the two electrodes. Whether a partner electrode in the fitting group exists may be determined upon applying a known stimulus to the electrode array.

The sound processing circuitry may also be adapted to derive a waveform having a frequency that is related to a computed frequency for each channel. The computed frequency may correspond to the stimulation frequency or may be calculated using more conventional methods, such as determining the instantaneous frequency. For example, the waveform may have a frequency that is equal to the computed frequency and may have a modulation depth that decreases as the computed frequency increases. Alternatively, the waveform may have a frequency that is proportional to the computed frequency. Such a waveform may be used as a carrier for presenting temporal information in each channel. The stream of pulse sets applied to each subset of electrodes may be derived from a current that may be modified based partly on such a carrier. Deriving such a carrier allows for improved time detection for presenting such temporal information.

The systems and methods described herein may provide improved frequency computation for presenting spectral information in sound processing strategies that can be used with cochlear implant systems that utilize simultaneous stimulation of several electrodes.

The systems and methods described herein may additionally or alternatively provide fitting sound processing strategies for such cochlear implant systems.

The systems and methods described herein may additionally or alternatively provide improved time detection for presenting temporal information in sound processing strategies that can be used with such cochlear implant systems.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 2 shows a spectral representation of a sound signal;

FIG. 3 shows an impulse train approximating the representation of FIG. 2;

Throughout the drawings, identical reference numbers designate similar, but not necessarily identical, elements.

DETAILED DESCRIPTION

Figure 1:
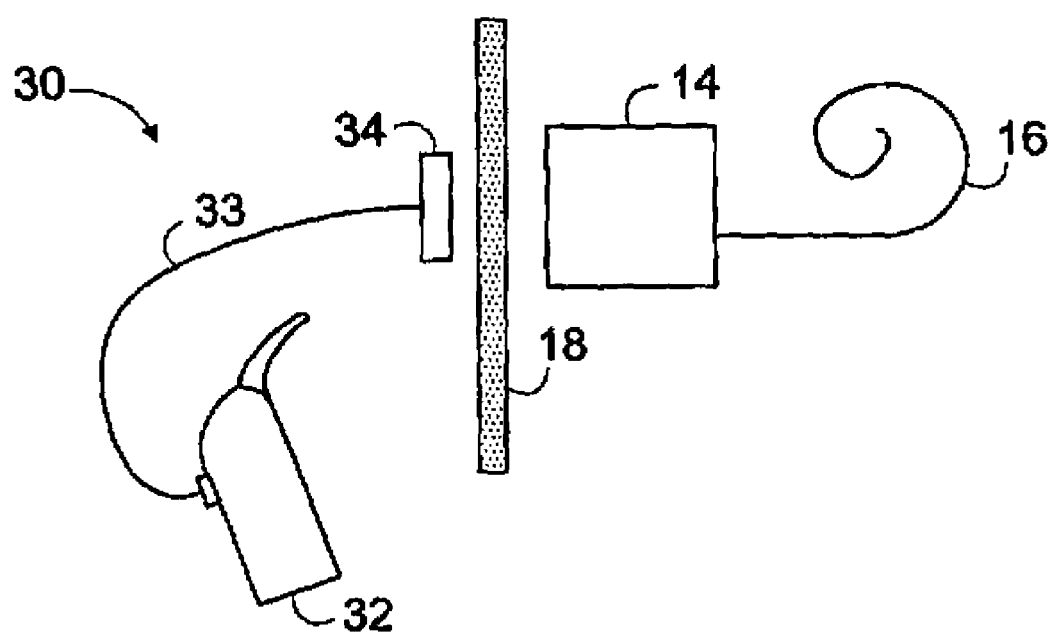
FIG. 1 shows several main components of a cochlear implant system.

FIG. 1 shows a representative block diagram of a cochlear implant system 30 that may be used in accordance with the systems and methods described herein. Cochlear implant system 30 may include unit 32, portion 34, device 14 and array 16. Unit 32 and portion 34 may be coupled through cable 33 and may be external portions of cochlear implant system 30. Device 14 and array 16, on the other hand, may be implanted into a patient. The external and internal portions may be separated by barrier 18, such as a layer of skin. Alternatively, cochlear system 30 may be a fully implantable system whereby devices performing the functions of unit 32 and portion 34 are internal.

Unit 32 may be a behind the ear ("BTE") unit that may be designed to be worn behind the ear of its user. Unit 32 may include a power source, a microphone, telemetry transmitter circuitry, as well as other sound processing components. Alternatively, unit 32 may be a portable speech processor (PSP) that may worn anywhere on the user. In such a situation, unit 32, may include a power source and sound processing components whereas portion 34 may include a microphone. Portion 34 may be a headpiece that houses an antenna coil. Device 14 may include an implantable receiver circuit for generating stimulation currents and a cochlear stimulator ("ICS") for selectively stimulating electrode array 16. Electrode array 16 may include several linearly aligned electrodes 66 (not shown in FIG. 1 but shown in FIGS. 3-5 and 9) and may be inserted within a user's cochlea.

In operation, sound may enter system 30 through the microphone in unit 32 which may deliver it to the sound processing components as an electrical signal. The sound processing components may process the signal and deliver it via cable 33 to portion 34. Portion 34 may in turn transmit the processed signal through telemetry transmitter circuitry to an implantable receiver circuit in device 14 through barrier 18. Device 14 may use the received signal to stimulate the electrodes in electrode array 16 in order to stimulate the user's auditory nerve. More thorough descriptions of certain aspects of elements 32, 33, 14 and 16 may be found, for example, in U.S. Pat. Nos. 4,819,647, 5,603,726, 5,603,726, 5,776,172, 6,129,753, 6,181,969, 6,219,580, 6, 289,247, 6,308,101, and U.S. patent application Ser. No. 11/058,848, filed Feb. 15, 2005, which are incorporated herein by reference in their entireties.

FIG. 2 shows a portional representation of a sound signal that may enter system 30 of FIG. 1. The frequency domain representation may have, for example, spectrum 26 as shown in FIG. 2. FIG. 3 shows a corresponding representation of the sound signal shown in FIG. 2 based on an embodiment of a stimulation strategy. More specifically, simultaneous stimulation of groups of electrodes 66 in electrode array 16 may generate an impulse train response at select frequencies that relatively mimics spectrum 26. Such a strategy takes advantage of the cochlear frequency/location correspondence described above. Such a strategy also takes advantage of the recent showings that simultaneous stimulation of adjacent electrodes results in virtual electrode stimulation, also as described above.

For example, stimulating the first pair of electrodes 66 with a first current level split between the pair, while assigning more relative weight—i.e., a higher portion of a current—to second electrode 66 than first electrode 66, may result in generating first impulse 35 at a particular frequency. First impulse 35 may correspond to a stimulus of a virtual electrode at a location corresponding to that frequency with a first current level.

Similarly, stimulating the second pair of electrodes 66 with a second current level split between the pair, while assigning more relative weight to second electrode 66 than third electrode 66, may result in generating second impulse 35 at a particular frequency. Second impulse 35 may correspond to a stimulus of a virtual electrode at a location corresponding to that frequency with the second current level.

Stimulating the third pair of electrodes 66 with a third current level split between the pair, while assigning more relative weight to fourth electrode 66 than third electrode 66, may result in generating third impulse 35 at a particular frequency. Third impulse 35 may correspond to a stimulus of a virtual electrode at a location corresponding to that frequency with the third current level.

Stimulating the fourth pair of electrodes 66 with a fourth current level split between the pair, while assigning more relative weight to fourth electrode 66 than fifth electrode 66, may result in generating fourth impulse 35 at a particular frequency. Fourth impulse 35 may correspond to a stimulus of a virtual electrode at a location corresponding to that frequency with the fourth current level.

The foregoing includes examples of simultaneous stimulation of pairs of adjacent electrodes. Although the following discussion and corresponding drawings relate to simultaneous stimulation of pairs of adjacent electrodes, the present systems and methods are not limited thereto. For example, two or more electrodes that may or may not be adjacent to one another may be simultaneously stimulated in order to stimulate a virtual electrode at a desired frequency/location.

FIGS. 4-7 and 9-12 show circuitry and processes that implement sound processing strategies for computing, among other things, stimulation frequencies—i.e., the frequencies that may be associated with optimal virtual electrodes. Stimulating an optimal virtual electrode at a location along the electrode array may be achieved by simultaneously stimulating surrounding electrodes. The circuitry and processes shown in FIGS. 4-7 and 9-12 may be implemented by electronic circuitry that is mostly part of the external portions of cochlear implant system 30 of FIG. 1, such as unit 32. For example, unit 32 may have sound processing circuitry that includes Fast Fourier Transform ("FFT") circuitry 42, envelope detector 52, peak locator 54 and navigator 56 shown in FIGS. 4, 5, 9 and 12. Moreover, in some embodiments, the sound processing circuitry in unit 32 may also include other circuitry, such as carrier synthesizer 90 shown in FIGS. 9 and 12, frequency estimator 120 shown in FIG. 12. Furthermore, unit 32 may include other circuitry such as mapper 58 of FIGS. 5, 9 and 12 as well as an automatic gain control ("AGC") circuit (not shown) and at least one buffer (not shown). Alternatively, unit 32 or any other portion of cochlear system 30 may include a subset of the components of FIGS. 4, 5, 9 and 12, while the internal portion includes at least some of the remaining components. In alternative embodiments, the circuitry and processes shown in FIGS. 4-7 and 9-12 may be implemented by software that may be run using cochlear implant system 30.

As mentioned above, sound may enter system 30 through the microphone in unit 32. The microphone may provide an electrical signal that is representative of the sound. The resulting electrical signal may be sampled and passed through the AGC circuit, among other things, before being buffered and windowed. The signal may be sampled at a rate r that may be proportional to the Nyquist rate. Moreover, sampling rate r may be selected to be fast enough to allow for proper reconstruction of the temporal details of the signal. For example, sampling rate r may be set at 17400 Hz or any other appropriate rate. The AGC circuit, which may be a dual-action and programmable circuit, may equalize and compress the dynamic range of the electrical signal, thereby suppressing distortion while maintaining fidelity. The output of the AGC circuit may then be placed into the buffer. The buffer may have a length m that corresponds to the length of the FFT which, as discussed below, is performed by FFT circuitry 42 in order to compute the frequency spectrum of the signal at a predefined rate. This predefined rate may be related to the envelope update rate which is discussed below.

The number of new samples that have been placed in the buffer since the last frequency spectrum computation may be tracked. If this number reaches a threshold value, the signal may be windowed and a new FFT computation may be initiated. The threshold value may relate to the rate at which the frequency spectrum is computed. For example, if the FFT for the signal is computed every 10 samples, then the threshold value may be set at 10 samples. The signal may be windowed in order to suppress glitches and avoid potential broadening of the frequency spectrum. During the windowing operation, each sample in the buffer may be multiplied by a predetermined weight and stored into another buffer. In some examples, if w[j] refers to the window function that is applied, and s[t] refers to the output of the AGC circuit, then:

$$s_w[j]=s[t-(m-1)+j]\cdot w[j]$$

The window function that is applied may be a Hamming window, a Hanning window, a Blackman window, a Kaiser window, any combination, such as a weighted sum, of the same or any other suitable window function. The window function typically has a peak at a main lobe about which the window is symmetric, and tapers on both sides thereby forming smaller side lobes. In some examples, the window function coefficients are chosen by trading off the bandwidth of function's main lobe and the height of its side lobes. For example, the window function may be chosen as an average between a Hanning window and a Blackman window, thereby resulting in side lobes that are approximately 45 dB below the function's peak.

Figure 4:
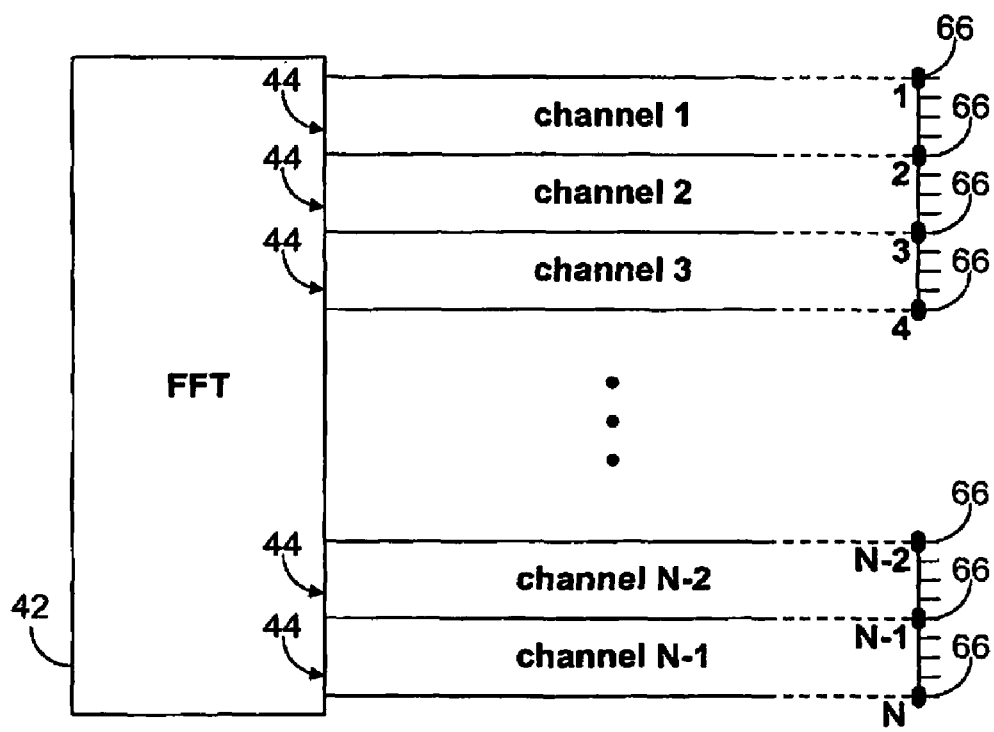
FIG. 4 shows a schematic for processing of sound.

The frequency spectrum of the signal that may have been buffered and windowed may be computed by through a time-to-frequency domain transformation. That may be accomplished by computing the Discrete Fourier Transform of the signal. The Discrete Fourier Transform may be computed through an FFT algorithm. Referring to FIG. 4, FFT circuitry 42 may implement such an algorithm, thereby computing the Discrete Fourier Transform of the signal as an m point FFT. The FFT may be chosen to be of any appropriate length m—i.e., number of samples—such as 256 samples. The frequency spectrum computation produces a representation of the signal that is broken down into frequency bins. In some examples, if $i_{bin}$ refers to the bin index—i.e., $i_{bin}=0, \ldots,$ (m−1)—and $F[i_{bin},t]$ refers to the Discrete Fourier Transform computed by FFT circuitry 42, while $IF[i_{bin},t]$ refers to the inverse Discrete Fourier Transform, then:

$$F[i_{bin}, t] = 1/m \sum_{i=0}^{m-1} s_w[i] \cdot \cos\left(2\pi \cdot \frac{i_{bin}}{m} \cdot i\right)$$

$$IF[i_{bin}, t] = 1/m \sum_{i=0}^{m-1} s_w[i] \cdot \sin\left(2\pi \cdot \frac{i_{bin}}{m} \cdot i\right)$$

The resulting frequency bins may be organized into a number of channels such that the frequency band associated with each channel includes a set of consecutive bins. Each channel may therefore correspond to a range of frequencies that lie within the computed frequency spectrum. The number of channels may depend on, among other things, the number of electrodes in the electrode array and the desired level of spectral resolution. For example, a stimulation strategy that uses an N-electrode array may lend itself to dedicating a single channel to each unique pair of electrodes, thereby yielding a total of N−1 channels, as shown in FIG. 4. In this example, channel 1 may be associated with the lowest frequency bins and may be dedicated to first and second electrodes 66, assuming the first electrode to be the one that is closest to the apex of the cochlea. Similarly, channel 2 may be associated with bins of higher frequency and may be dedicated to second and third electrodes 66. Also, channel 3 may be associated with bins of even higher frequency and may be dedicated to third and fourth electrodes 66. Likewise, channel N−1 may be associated with the highest frequency bins and may be dedicated to $(N-1)^{st}$ and $N^{th}$ electrodes 66, assuming the $N^{th}$ electrode to be the one that is closest to the basal end of the cochlea. Each channel may therefore define the relationship of a set of consecutive bins over an electrode pair. A virtual electrode may be stimulated by exciting an adjacent pair of bounding electrodes simultaneously while assigning different relative weights applied to them, as exemplified in and discussed in connection with FIG. 2. The following discussion in connection with FIG. 5 further details this strategy.

Figure 5:
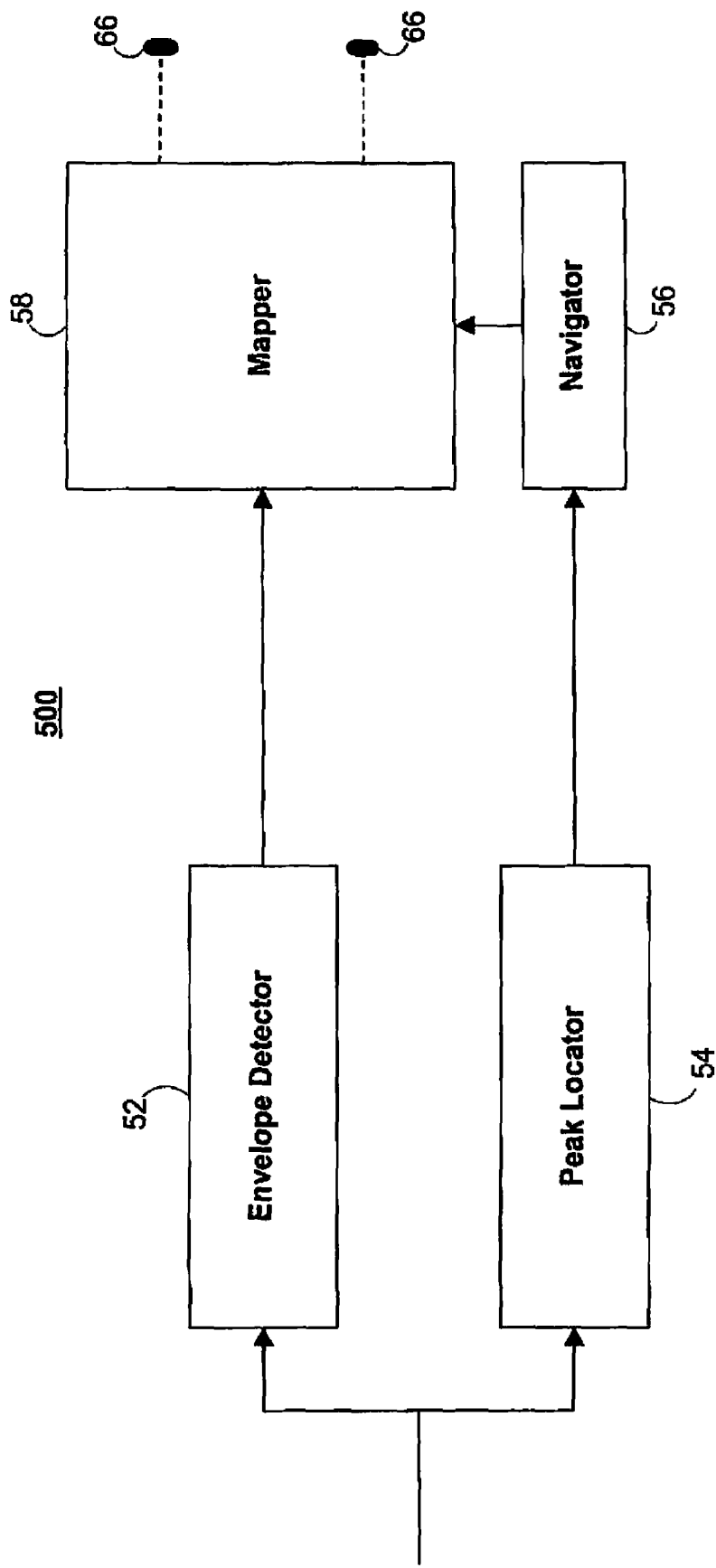
FIG. 5 shows a block diagram of sound processing circuitry.

FIG. 5 shows a collection of components that may be referred to as subsystem 500. Such a subsystem may be used to stimulate an optimal virtual electrode using a pair of adjacent electrodes 66 for at least one channel 44 of FIG. 4. Each set of frequency bins associated with a channel may be provided as input to subsystem 500. Accordingly, subsystem 500 may be applied to any channel. The processing circuitry in cochlear system 30 of FIG. 1 may include several instances of subsystem 500. For example, such processing circuitry includes N−1 iterations of subsystem 500 in order for all subsystem to be applied to all channels simultaneously. Each pair of electrodes may however be stimulated without stimulating any other electrodes in the array. Accordingly, in an alternative embodiment, each pair of electrodes may be stimulated sequentially whereby each channel may be applied to the same subsystem 500. In such an embodiment, only one iteration of subsystem 500 would be included in the processing circuitry.

Different groups of electrode pairs that are separated by a sufficient number of electrodes so as to avoid undesirable electrode interference may be stimulated simultaneously. This may increase the stimulation speed by achieving an effective stimulation rate. For example, in a system that uses 17 electrodes, hence 16 channels, four iterations of subsystem 500 may be used. In this case, there may be four multiplexed stimulation periods. In the first period, the first subsystem may be associated with channel 1 and coupled to electrodes 1 and 2, the second subsystem may be associated with channel 2 and coupled to electrodes 5 and 6, the third subsystem may be associated with channel 3 and coupled to electrodes 9 and 10 and the fourth subsystem may be associated with channel 4 and coupled to electrodes 13 and 14. In the second period, the first subsystem may be associated with channel 5 and coupled to electrodes 4 and 5, the second subsystem may be associated with channel 6 and coupled to electrodes 8 and 9, the third subsystem may be associated with channel 7 and coupled to electrodes 12 and 13 and the fourth subsystem may be associated with channel 8 and coupled to electrodes 16 and 17. In the third period, the first subsystem may be associated with channel 9 and coupled to electrodes 3 and 4, the second subsystem may be associated with channel 10 and coupled to electrodes 7 and 8, the third subsystem may be associated with channel 11 and coupled to electrodes 11 and 12 and the fourth subsystem may be associated with channel 12 and coupled to electrodes 15 and 16. Finally, in the fourth period, the first subsystem may be associated with channel 13 and coupled to electrodes 2 and 3, the second subsystem may be associated with channel 14 and coupled to electrodes 6 and 7, the third subsystem may be associated with channel 15 and coupled to electrodes 10 and 11 and the fourth subsystem may be associated with channel 16 and coupled to electrodes 14 and 15. In such an arrangement, four groups of electrode pairs separated by at least two electrodes may be stimulated in each stimulation period such that the entire array of 17 electrodes is stimulated in four consecutive periods using four iterations of subsystem 500 for 16 channels.

Subsystem 500 of FIG. 5 may include envelope detector 52, peak locator 54, navigator 56 and mapper 58. The functions performed by these and other components, such as those shown in FIGS. 4, 9 and 12 may alternatively be performed through software. Envelope detector 52 may apply an envelope detection algorithm to a channel. For example, a Hilbert transform may be applied to the input signal. The Hilbert transform may be computed using the real and imaginary parts of the input signal. The envelope of the signal may then be computed based on the Hilbert transform. The envelope may be a Hilbert envelope computed as the square root of the sum of the squared imaginary parts and the squared real parts. In some examples, if $i_{start}$ and $i_{end}$ denote the bin boundaries of each channel, $H_r[\tau,t]$ refers to the real part of the Hilbert transform while $H_i[\tau,t]$ refers to the imaginary part of the Hilbert transform and HE[t] refers to the computed envelope, then:

$$H_r[\tau, t] = \sum_{k=i_{start}}^{i_{end}} F[k, t] \cdot \cos\left(\frac{2\pi}{m}k\tau\right) - IF[k, t] \cdot \sin\left(\frac{2\pi}{m}k\tau\right)$$

$$H_i[\tau, t] = \sum_{k=i_{starti}}^{i_{end}} F[k, t] \cdot \sin\left(\frac{2\pi}{m}k\tau\right) + IF[k, t] \cdot \cos\left(\frac{2\pi}{m}k\tau\right)$$

$$HE[t] = \sqrt{H_i[t]^2 + H_r[t]^2}$$

The logarithm of envelope HE may be computed directly on the sum of the squares in order to avoid computing the square root of the sum. The envelope update rate for the channel—i.e., the rate at which the envelope should be computed—may correspond to the channel bandwidth. The channel bandwidth may be proportional to the number of bins in the channel multiplied by the bin width. The bin width may be equal to the sampling rate r divided by the length m of the FFT. In some examples, the proportionality factor is the same as that used for over-sampling. Accordingly, if o is the over-sampling factor—e.g., the ratio between the sampling rate r and the Nyquist rate—the envelope update rate for a channel may be equal to the number of bins in the channel multiplied by o.r/m.

In practice, computing the envelope for a channel may be computationally prohibitive, especially for wide channels. To solve this problem, envelope detector 52 may implement process 600 illustrated in FIG. 6 so that the envelope may be more easily computed for a channel. At step 610, a channel may be broken into sub-channels. Each of the sub-channels may have a bandwidth for which envelope computation is not prohibitive. In some examples, each of the sub-channels may have a bandwidth that is less than or equal to the sampling rate r divided by the over-sampling factor o. At step 620, the envelope for each sub-channel is derived. The envelope may be derived by computing the Hilbert envelope for each sub-channel, as described above. At step 630, the envelope for the entire channel is computed as the root-mean square of the envelopes of the sub-channels. More specifically, the envelope may be computed as the square root of the sum of the squared envelopes computed for each sub-channel. Process 600 may be applied to one or more channels. For example, process 600 may apply to the widest channel, or alternatively, to a subset of channels for which traditional envelope computation may be considered computationally challenging.

Figure 7:
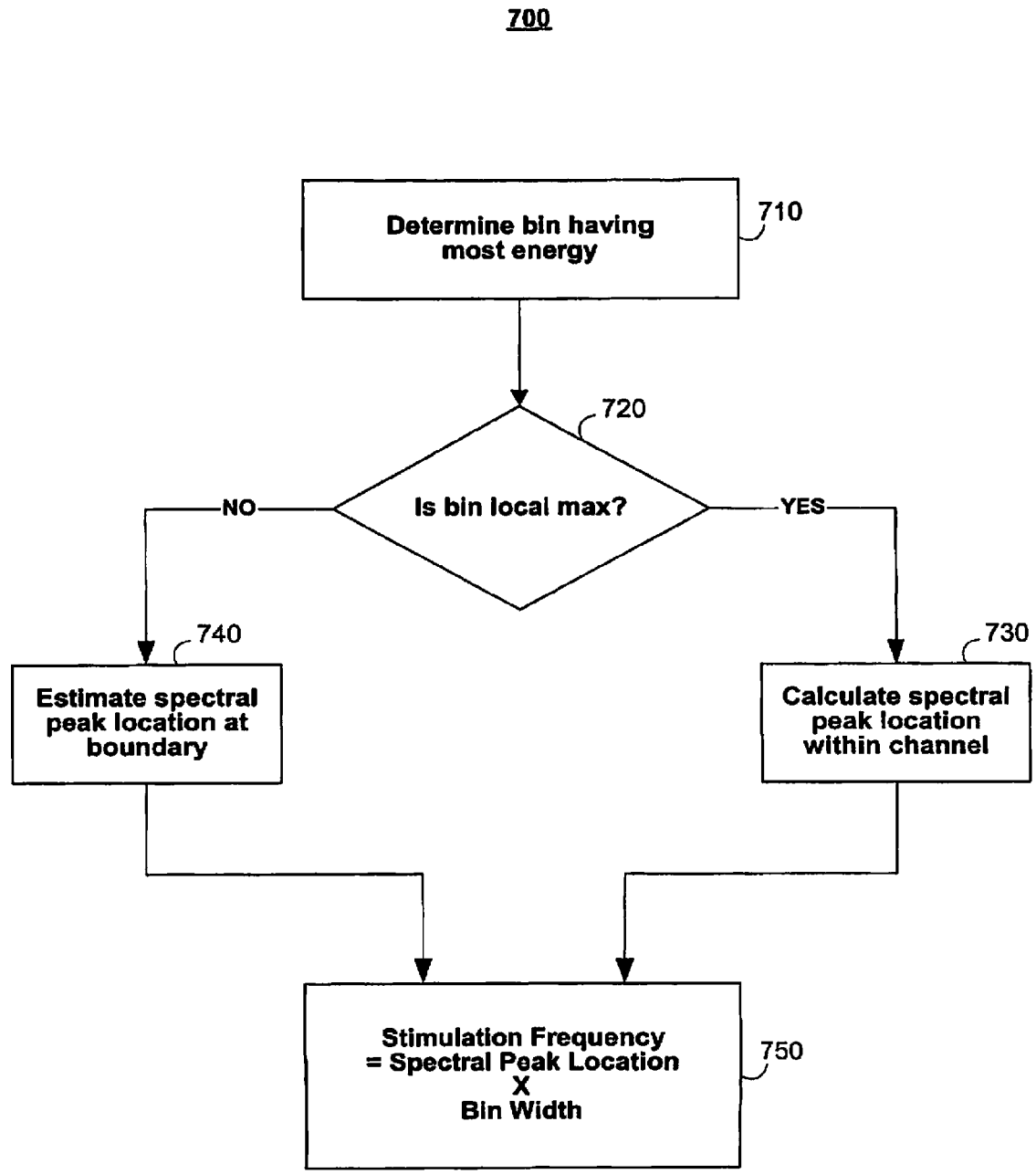
FIG. 7 shows another flow diagram for processing sound.

In some embodiments, the stimulation frequency for a channel may be computed as the frequency at which the spectral peak is located—i.e., the frequency at which the signal has the highest amplitude—in the channel. Peak locator 52 of FIG. 5 may be used to calculate such a frequency. FIG. 7 illustrates a process 700 that may be implemented by peak locator 52 in order to calculate such a frequency for a channel.

At step 710, the bin having the most energy in the channel is determined. That may be achieved by computing the energy in each bin in the channel and comparing the computed bin energies. Bin energy may be computed by taking the sum of the square of the real and imaginary parts of the input signal. At step 720, a determination is made as to whether the bin with the most energy corresponds to a local maximum over the entire spectrum. Whether the bin with the most energy is a local maximum may be determined by determining whether the computed energy for that bin is larger or equal to the computed energies for adjacent bins.

If it is determined that the bin with the most energy is a local maximum at step 720, then the spectral peak location is calculated at step 730. The spectral peak location may be set to be the location of a point within the bin that has the most energy or within neighboring bins. Such a point may be located in the middle of the bin that has the most energy. In alternative embodiments, the spectral peak location may be calculated by fitting a function between a group of points that lie within the bin that has the most energy and within neighboring bins, and computing the location at which the maximum of the function exists. Such a function may be chosen based on the window function w[j]. For example, in the situation where the window function is a weighted sum of a Hanning and a Blackman window, the spectral peak location may be calculated by fitting a parabola between the amplitude of the bin that has the most energy and the amplitudes of the two neighboring bins. In some examples, if $i_{peak}$ is the index of the bin corresponding to the local maximum and k refers to the spectral peak location, then:

$$k = \frac{|F[i_{peak}+1]|^2 - |F[i_{peak}-1]|^2}{2\cdot(|F[i_{peak}+1]|^2 + |F[i_{peak}-1]|^2 - 2\cdot|F[i_{peak}]|^2)} + i_{peak}$$

More accurate results may be obtained by computing the logarithm of the amplitudes of the chosen bins, although such calculations may be more computationally intensive. For example, the spectral peak location may be calculated as:

$$k = \frac{\log|F[i_{peak}+1]| - \log|F[i_{peak}-1]|}{2\cdot(\log|F[i_{peak}+1]| + \log|F[i_{peak}-1]| - 2\log\cdot|F[i_{peak}]|)} + i_{peak}$$

If it is determined that the bin with the most energy is not a local maximum at step 720, then spectral peak location is estimated at step 740. The spectral peak location k may be set to be the location of a point that lies midway between that bin and whichever of the two neighboring bins has the larger energy. This may be based on the approximation that the spectral peak is located near the boundary of the channel. In this situation, the spectral peak location may be estimated from the following:

$$k = \begin{cases} i_{peak} - 0.5 & F[i_{peak}-1] > F[i_{peak}] \\ i_{peak} + 0.5 & F[i_{peak}+1] > F[i_{peak}] \end{cases}$$

After the spectral peak location is obtained in either step 730 or step 740, it is translated into frequency at step 750. The frequency at which the spectral peak is located within a channel may be computed by multiplying the spectral peak location by the bin width r/m. The computed stimulation frequency may correspond to the frequency at which the spectral peak is located. The Thus, if $f_s$ refers to the stimulation frequency, then:

$$f_s = k*r/m$$

Peak location may be computed at a rate that is proportional to the bin width. In some examples, the proportionality factor is equal to the over-sampling factor o. Accordingly, peak locator 52 may be used to compute the stimulation frequency at a rate of o·r/m.

After the stimulation frequency for a channel is calculated, such a frequency may be translated into a desired cochlear location—i.e., the corresponding physical location along the electrode array that may be associated with that frequency. This may be accomplished by interpolating the cochlear location from a frequency-to-location table, which was mentioned above. More particularly, the frequency-to-location table may map each bin to a physical location along the electrode array. In some examples, if FtL[i] refers to function that performs such mapping and l refers to the desired cochlear location corresponding to the stimulation frequency for a channel, then:

$$l = F2L[i_{peak}] + \begin{cases} (F2L[i_{peak}+1] - F2L[i_{peak}])\cdot(k - i_{peak}) & k > i_{peak} \\ (F2L[i_{peak}] - F2L[i_{peak}-1])\cdot(k - i_{peak}) & k \le i_{peak} \end{cases}$$

A pair of adjacent electrodes may be stimulated using relative current weights in order to stimulate the optimal virtual electrode at the desired cochlear location corresponding to the computed stimulation frequency for a channel. After the desired cochlear location is determined, navigator 56 of FIG. 5 may translate such a location into weights assigned to a current that may be applied to each electrode in order to stimulate the virtual electrode at the desired cochlear location. The weighted currents may be transmitted to electrode array 16 through device 14 of FIG. 1.

More specifically, navigator 52 may compute weight w that may be associated with the second electrode in an electrode pair, while the first electrode is associated with weight 1−w. In some examples, if $l_0$ refers to the nominal location of the first electrode, then:

$$w = 1 - l_0$$

Navigator 56 may also round the computed location to the nearest allowable cochlear location. In addition, navigator 56 may also ensure that stimulation does not exceed the boundaries of the channel. In some examples, navigator 56 applies the following constraint:

$$w = \begin{cases} 0 & w < 0 \\ 1 & w > 1 \\ w & \text{otherwise} \end{cases}$$

Moreover, navigator 56 may ensure that, in the event that one of the electrodes in a pair of electrodes to be stimulated is disabled, all of the current is applied to the other electrode. This may be useful during the fitting discussed below. In some examples, if E1 and E2 refer to the first and second electrodes in an electrode pair, respectively, navigator 56 may apply the following constraint:

$$w = \begin{cases} 0 & E2 \text{ disabled} \\ 1 & E1 \text{ disabled} \\ w & \text{all channels enabled} \end{cases}$$

Mapper 58 of FIG. 5 may receive the outputs of each of envelope detector 52 and navigator 56. Mapper 58 may derive from these inputs streams of pulse sets that may be applied to an electrode pair for a channel to stimulate that pair. More specifically, mapper 58 may modify a current based on the envelope computed by envelope detector 52 and split the current between the electrode pair based on the relative weights computed by navigator 56 for a channel. In some examples, if M1 and M2 refer to the mapping functions applied to the first and second electrodes in the electrode pair for the channel, then currents I1 and I2 applied to the first and second electrodes may be computed as follows:

$$I2 = M2(\max(HE))\cdot w$$

$$I1 = M1(\max(HE))\cdot(1-w)$$

max(HE) refers to the largest envelope value computed using envelope detector 52 for the channel, in case the stimulation rate is slower than the envelope update rate. In case the stimulation rate is faster than the envelope update rate, the most recently computed envelope value may used. Applying currents I1 and I2 simultaneously to electrodes E1 and E2 respectively may stimulate a virtual electrode at a location along the cochlear array that corresponds to the frequency at which a spectral peak is located within a particular channel. Envelope detection, peak location and weight computation may be applied to each channel in order to stimulate all possible electrode pairs through currents derived through one or more mappers across the entire sound spectrum for which the FFT is computed.

The above equations relating to the currents applied to electrodes E1 and E2 may be particularly suitable if the electrical fields resulting from the stimulation of these electrodes interact strongly such that the loudness perceived by the user is appropriate. However, if such an interaction is weaker at a location corresponding to the stimulation frequency such that the perceived loudness is lower, the above equations may be modified so as to compensate for such loss in loudness. More specifically, I1 and I2 may be multiplied by a factor that increases as w increases from 0 to 0.5 or as w decreases from 1 to 0.5. Such a factor may be empirically determined based on user response to perceived loudness. Such a factor may equal 1 near w=0 and w=1.

Figure 8:
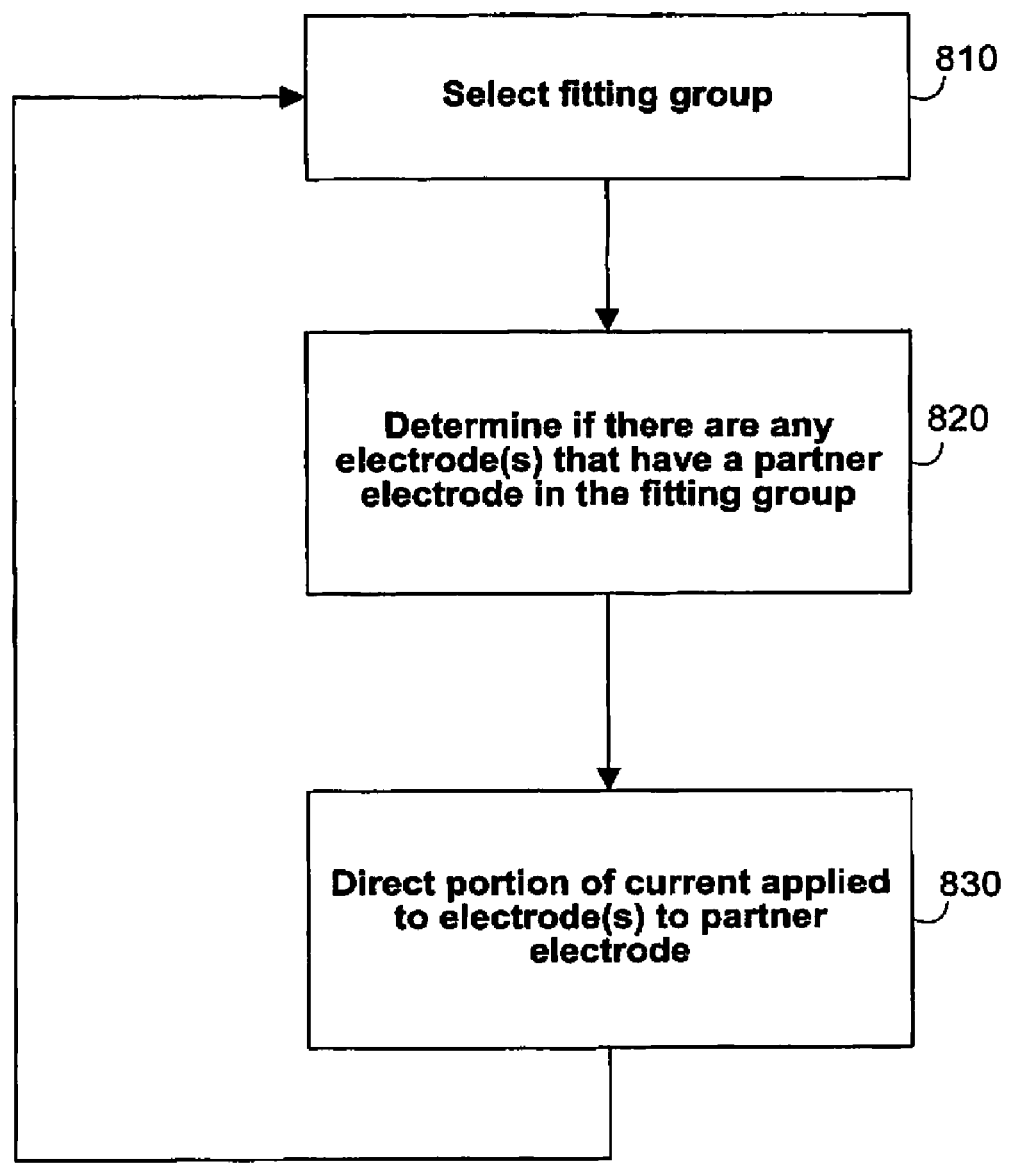
FIG. 8 shows a flow diagram for fitting sound processing strategies.

As mentioned above, it would be desirable to devise a method for fitting sound processing strategies such as ones that utilize simultaneous stimulation of electrodes. FIG. 8 illustrates process 800 for performing such fitting. Process 800 may be applied to one group of electrodes at a time.

At step 810, a group of electrodes known as a fitting group is selected. The fitting group may include 4 or 5 electrodes but may include any desired number of electrodes. For each electrode that is not included in the fitting group, a determination as to whether a partner electrode for that electrode exists in the fitting group is made at step 820. A partner electrode is an electrode that would be stimulated simultaneously with the electrode in question—i.e., an electrode whose electric field would be superposed to that of the electrode in question so as to stimulate a virtual electrode when the electrode in question and its partner electrode are stimulated simultaneously. Such a partner electrode may typically be located relatively close to the electrode in question. A known sound stimulus to which the patient is comfortable may be applied to the patient's cochlear system in order to help determine whether a partner electrodes exist at step 820. The determination at step 820 may be based on whether the electrodes are defined as partner electrodes or assigned to the same channel for simultaneous stimulation. Alternatively, the determination may be based on whether the user's perception of sound changes when the partner electrode is enabled and the stimulus is applied. For a stimulation strategy that utilizes simultaneous stimulation of pairs of adjacent electrodes, the electrode in the fitting group would be considered a partner electrode to the electrode(s) adjacent to it.

If a partner electrode exists in the fitting group, then the portion of the current that would otherwise be applied to the electrode in question is directed to the partner electrode at step 830. This may be made possible by disabling all electrodes in the electrode array that are not part of the fitting group because navigator 56 of FIG. 5 may ensure that all of the current otherwise applied to disabled electrodes is instead applied to its partner electrode, as discussed above. This may be repeated for other fitting groups having at least another electrode as process 800 reverts back to step 810 from step 830 until all desired fitting groups are selected. Process 800 may result in an accurate estimation of the current level required for each electrode because the loudness generated by splitting a current between at least one electrode and its partner electrode(s) is approximately equal to the loudness generated by applying the entire current to the at least one electrode.

Figure 9:
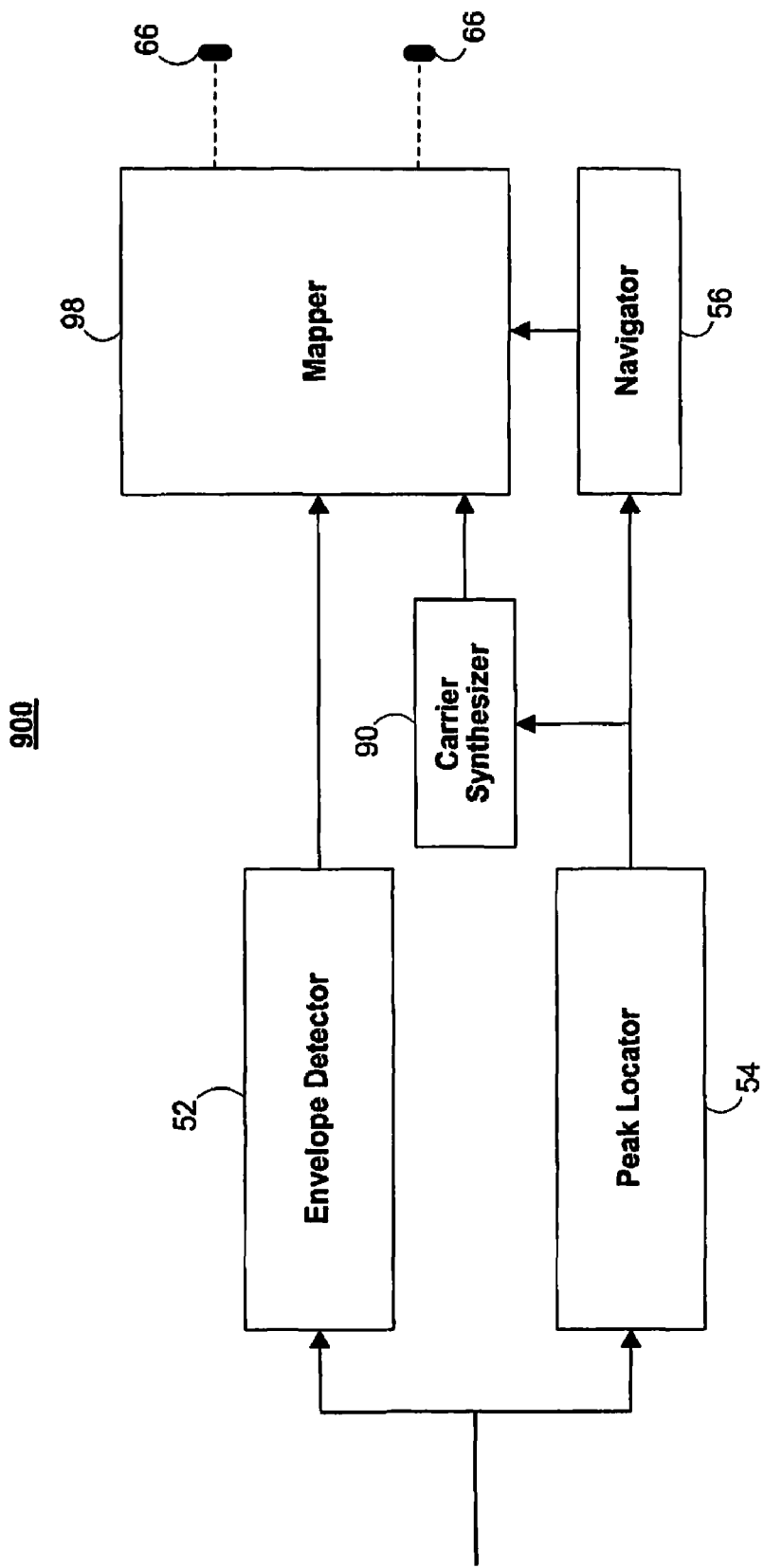
FIG. 9 shows a block diagram of an alternative embodiment of sound processing circuitry.

FIG. 9 shows a collection of components that may be referred to as subsystem 900. Subsystem 900 may be an alternative embodiment of a subsystem that may be used to stimulate an optimal virtual electrode using a pair of adjacent electrodes 66 for at least one channel 44 of FIG. 4. Like subsystem 500, subsystem 900 may be applied to each channel, whereby each set of frequency bins associated with a channel may be provided as input to subsystem 900. The processing circuitry in cochlear system 30 of FIG. 1 may include one or more instances of subsystem 900. For example, such processing circuitry may include a single subsystem 900. As another example, the processing circuitry in a cochlear system that that utilizes N electrodes may include N−1 iterations of subsystem 900 in order for such a subsystem to be applied to all channels simultaneously. Alternatively, such processing circuitry may include any other number of iterations of subsystem 900 such that different groups of electrode pairs are stimulated simultaneously so as to achieve an effective pulse repetition rate. Such electrode pairs may be separated by a sufficient number of electrodes so as to avoid undesirable electrode interference.

Figure 6:
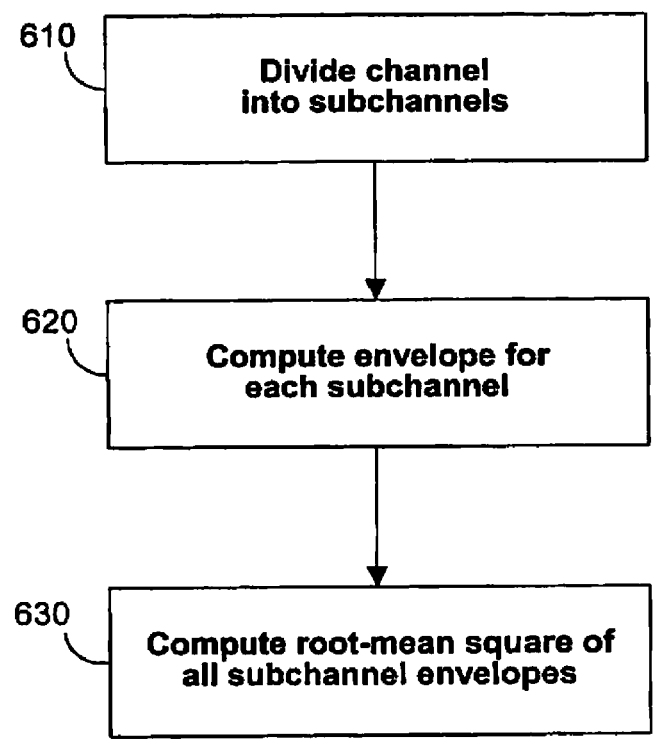
FIG. 6 shows a flow diagram for processing sound.

Like subsystem 500, subsystem 900 may include envelope detector 52, peak locator 54 and navigator 56, which were discussed in connection with FIGS. 5-7. Envelope detector 52 may apply an envelope detection algorithm to a channel from which envelope HE may be computed. Peak locator 54 may be used to locate the frequency at which the spectral peak is located within a channel and therefore compute the corresponding cochlear location along the electrode array. Navigator 56 may translate such a location into weights w and (1-w) that may be assigned to a current applied to each electrode in order to stimulate the virtual electrode at the desired cochlear location.

As mentioned above, it is desirable to present temporal information in sound processing strategies such as ones that utilize simultaneous stimulation of electrodes. Carrier synthesizer 90, which may also be included in subsystem 900, may be used to derive carrier c in order to present such temporal information. Carrier synthesis may be performed at a rate that is equal to the frame rate FR—i.e., the rate at which individual channels may be updated.

Figure 12:
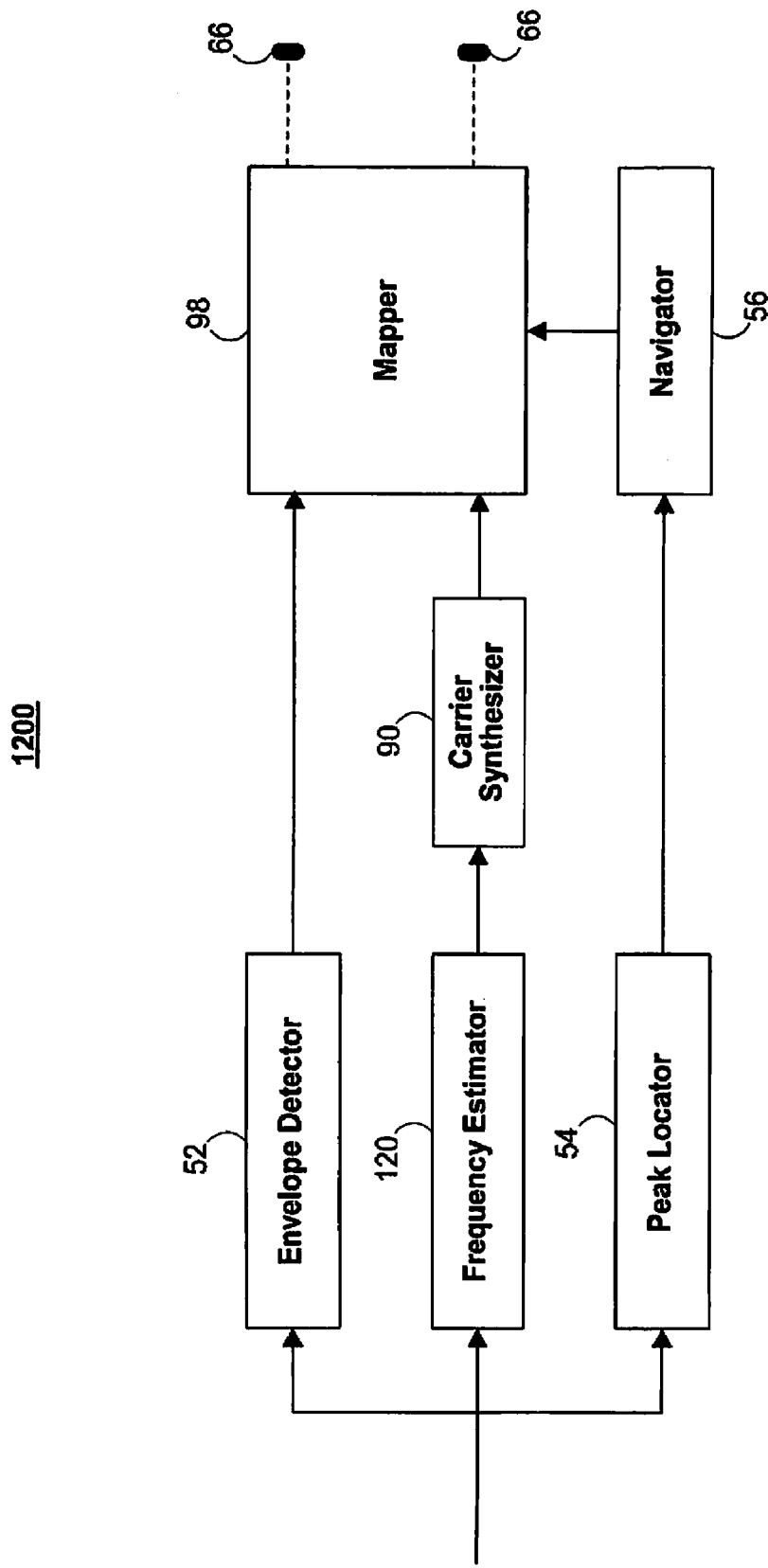
FIG. 12 shows a block diagram of another alternative embodiment of sound processing circuitry.

The carrier may have a frequency that corresponds, or is proportional, to the stimulation frequency. As discussed above, such a frequency may be the one at which the spectral peak within a channel is located, as computed by peak locator 54. In an alternative embodiment, such a frequency may be computed using conventional methods. Such an embodiment is shown in FIG. 12 wherein a collection of components may be referred to as subsystem 1200. Like subsystems 500 and 900, subsystem 1200 may include envelope detector 52, peak locator 54 and navigator 56 and carrier synthesizer 90. Subsystem 1200 also includes frequency estimator 120 for estimating a frequency for the carrier. Frequency estimator may derive the carrier frequency by calculating the instantaneous frequency along with phase angle and magnitude values, as described in U.S. Pat. No. 6,480,820. For example, the instantaneous frequency may be calculated from the derivative of the phase.

Figure 10:
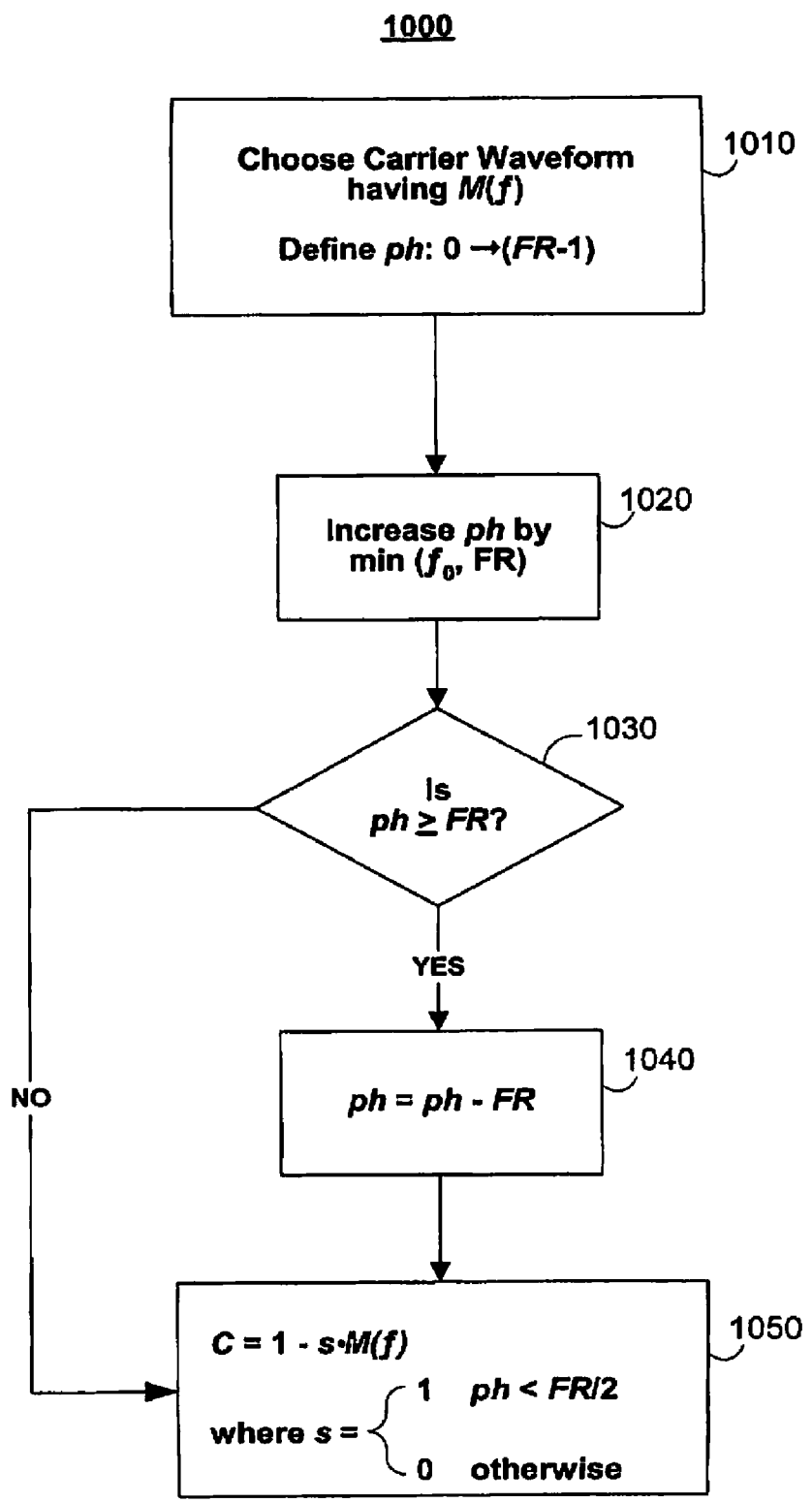
FIG. 10 shows yet another flow diagram for processing sound.

In some examples, the carrier may be derived using Gated Max Rate ("GMR") stimulation. In this process, carrier synthesizer 90 of FIG. 9 or 12 may produce a waveform having a frequency $f_o$ that may be equal to the frequency computed through peak locator 54 or frequency estimator 120. Although it would be desirable to utilize a half-wave rectified and filtered sinusoid as the carrier waveform, it may be more practical to utilize a square wave. The waveform may have a modulation depth that depends on $f_o$. For example, the waveform may have a modulation depth that decreases when $f_o$ is increased. FIG. 10 illustrates process 1000 which may be implemented by carrier synthesizer 90 to reconstruct a rectified sinusoidal waveform using GMR stimulation.

At step 1010, a carrier waveform is chosen. The carrier waveform may be chosen such that its modulation depth may be dependent on the frame rate FR. For example, the carrier waveform may be chosen such that its modulation depth decreases linearly with $f_o$, when $f_o$ lies within a particular range. In some examples, if M(f) refers to the modulation depth function, then:

$$M(f) = \begin{cases} 1 & f \leq FR/2 \\ 2 \cdot (1 - f/FR) & FR > f > FR/2 \\ 0 & f \geq FR \end{cases}$$

A carrier phase variable ph is also defined for each channel at step 1010. ph may range from 0 to FR-1. At step 1020, ph may be increased during each frame by the minimum of $f_o$ and FR. A determination as to whether ph is greater than or equal to FR is made at step 1030. If ph is greater than or equal to FR, then FR is subtracted from ph at step 1040. Otherwise, ph remains unchanged. At step 1050, the carrier c is computed as:

$$c = 1 - s \cdot M(f) \text{ where } s = \begin{cases} 1 & ph < FR/2 \\ 0 & \text{otherwise} \end{cases}$$

Figure 11:
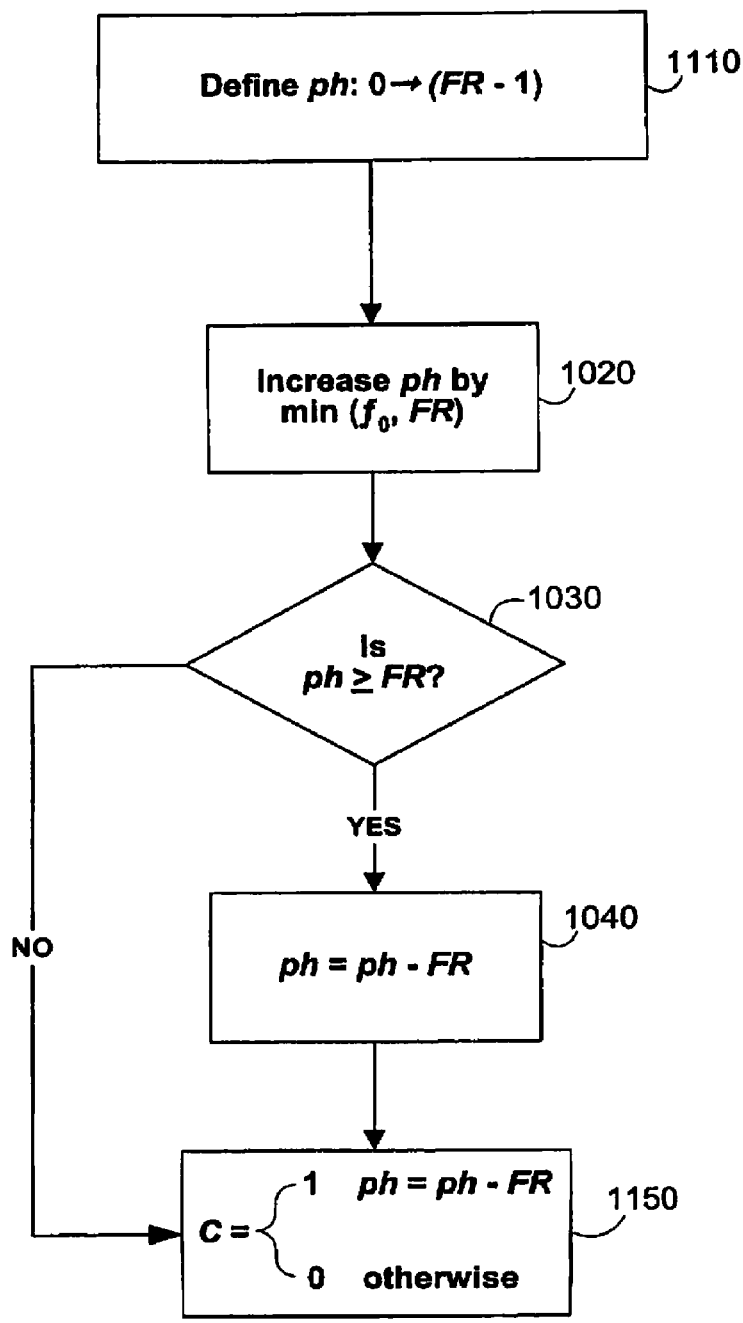
FIG. 11 shows an alternative embodiment of yet another flow diagram for processing sound.

In an alternative embodiment, the carrier may be derived using Frequency-Modulation Stimulation ("FMS"). In this process, carrier synthesizer 90 of FIG. 9 or 12 may produce a waveform having a frequency that is proportional to the frequency $f_o$ computed through peak locator 54 or frequency estimator 120. FIG. 11 illustrates process 1100 which is similar to process 1000 of FIG. 10 and which may be implemented by carrier synthesizer 90 to reconstruct a rectified sinusoidal waveform using FMS stimulation.

At step 1110, a carrier phase variable ph is defined for each channel. ph may range from 0 to FR*n-1. _n may be set at 0.5 or at any other appropriate value. At step 1020, ph may be increased during each frame by the minimum of $f_o$ and FR. A determination as to whether ph is greater than or equal to FR is made at step 1030. If ph is greater than or equal to FR, then FR is subtracted from ph at step 1040. Otherwise, ph remains unchanged. At step 1150, the carrier c is computed as:

$$c = \begin{cases} 1 & ph = ph - FR \\ 0 & \text{otherwise} \end{cases}$$

Subsystems 900 and 1200 of FIGS. 9 and 12 may also each include mapper 98, which may receive the outputs of each of envelope detector 52, navigator 56 and carrier synthesizer 90. Mapper 98 may derive from these inputs streams of pulse sets that may be applied to an electrode pair for a channel to stimulate that pair. More specifically, mapper 98 may modify a current based on the envelope and carrier derived by envelope detector 52 and carrier synthesizer 90, respectively, and split the current between the electrode pair based on the relative weights computed by navigator 56 for a channel. In some examples, if M1 and M2 refer to the mapping functions applied to the first and second electrodes in the electrode pair for the channel, then currents I1 and I2 applied to the first and second electrodes may be as follows:

$I2 = M2(\max(HE)) \cdot c \cdot w$ $I1 = M1(\max(HE)) \cdot c \cdot (1-w)$

Again, max(HE) refers to the largest envelope value computed using envelope detector 52 for the channel, in case the stimulation rate is slower than the envelope update rate. In case the stimulation rate is faster than the envelope update rate, the most recently computed envelope value may used. In some examples, mapping function M1 or M2 may be combined with carrier c prior to applying weight (1-w) or w. If the envelope has not been computed between the previous and the next computation, then the previous envelope value may used. Also, currents I1 and I2 may be modified in order to compensate for a decrease in perceived loudness at locations where electrical field interaction is relatively weak.

Applying currents I1 and I2 simultaneously to electrodes E1 and E2 respectively may present temporal information associated with the electrical signal representative of the sound in addition to stimulating a virtual electrode at a location along the cochlear array that corresponds to the frequency at which a spectral peak is located within a particular channel. Envelope detection, peak location, carrier synthesis and weight computation may be applied to each channel in order to stimulate all possible electrode pairs through currents derived through one or more mappers across the entire sound spectrum for which the FFT is computed.

The foregoing is merely illustrative of the principles of this invention and various modifications can be made by those skilled in the art without departing from the scope and spirit of the invention. For example, the number of channels into which FFT frequency bins may be organized may be a multiple of (N-1) in a stimulation strategy that uses an N-electrode array. If the multiplication factor is referred to as p, then a number of p channels may define the relationship of sets of consecutive bins in these channels over an electrode pair. For example, if p=2, then a pair of channels may define the relationship of two sets of consecutive bins in these channels over an electrode pair.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method for use in a cochlear implant system, the method comprising:
   computing a frequency spectrum of a signal representative of sound in order to produce a representation of the signal that is broken down into a plurality of frequency bins that are organized into a plurality of channels such that each channel comprises a subset of the plurality of bins;
   determining a bin that has the most energy out of a subset of the bins corresponding to a channel included within the plurality of channels;
   determining whether the energy in the bin is larger than energies in other bins adjacent to the bin;
   if the energy in the bin is larger than energies in the adjacent bins, computing a stimulation frequency corresponding to the channel to be a frequency that corresponds to a location of a point in the middle of the bin; and
   if the energy in the bin is not larger than energies in the adjacent bins, computing the stimulation frequency corresponding to the channel to be a frequency that corresponds to a location of a point that lies midway between the bin and another bin having the larger energy of the adjacent bins.

2. The method of claim 1, wherein the computing of the frequency spectrum comprises applying a Fast Fourier Transform to the signal representative of the sound.

3. The method of claim 1, wherein the determining of the bin that has the most energy comprises taking a sum of a square of a real part and an imaginary part of the input signal.

4. The method of claim 1, wherein the determining of whether the energy in the bin is larger than the energies in the other bins adjacent to the bin comprises computing a log of the bin and the other bins.

5. The method of claim 1, further comprising translating the stimulation frequency into a cochlear location.

6. The method of claim 5, wherein the translating comprises interpolating the cochlear location from a frequency-to-location table.

7. The method of claim 5, further comprising stimulating a pair of electrodes using relative current weights to stimulate a virtual electrode at the cochlear location.

8. A method for use in a cochlear implant system, the method comprising:
  computing a frequency spectrum of a signal representative of sound in order to produce a representation of the signal that is broken down into a plurality of frequency bins that are organized into a plurality of channels such that each channel comprises a subset of the plurality of bins;
  determining a bin that has the most energy out of a subset of the bins corresponding to a channel included within the plurality of channels;
  determining whether the energy in the bin is larger than energies in other bins adjacent to the bin; and
  if the energy in the bin is not larger than energies in the adjacent bins, computing a stimulation frequency corresponding to the channel to be a frequency that corresponds to a location of a point that lies midway between the bin and another bin having the larger energy of the adjacent bins.

9. The method of claim 8, wherein the computing of the frequency spectrum comprises applying a Fast Fourier Transform to the signal representative of the sound.

10. The method of claim 8, wherein if the energy in the bin is larger than energies in the adjacent bins, the method further comprises computing the stimulation frequency to be a frequency that corresponds to a location of a point in the middle of the bin.

11. The method of claim 8, wherein if the energy in the bin is larger than energies in the adjacent bins, the method further comprises computing the stimulation frequency to be a frequency that corresponds to a location of a maximum of a parabola that is fit between a plurality of points within the bin and two of the adjacent bins.

12. The method of claim 8, wherein the determining of whether the energy in the bin is larger than the energies in the other bins adjacent to the bin comprises computing a log of the bin and the other bins.

13. The method of claim 8, further comprising translating the stimulation frequency into a cochlear location.

14. The method of claim 13, wherein the translating comprises interpolating the cochlear location from a frequency-to-location table.

15. The method of claim 13, further comprising stimulating a pair of electrodes using relative current weights to stimulate a virtual electrode at the cochlear location.

16. A method for use in a cochlear implant system, the method comprising:
  computing a frequency spectrum of a signal representative of sound in order to produce a representation of the signal that is broken down into a plurality of frequency bins that are organized into a plurality of channels such that each channel comprises a subset of the plurality of bins;
  determining a bin that has the most energy from a subset of the plurality of bins in a channel;
  determining whether the energy in the bin is larger than energies in other bins adjacent to the bin;
  if the energy in the bin is larger than energies in the adjacent bins, computing a stimulation frequency to be a frequency that corresponds to a location of a maximum of a parabola that is fit between a plurality of points within the bin and two of the adjacent bins; and
  if the energy in the bin is not larger than energies in the adjacent bins, computing the stimulation frequency to be a frequency that corresponds to a location of a point that lies midway between the bin and another bin having the larger energy of the adjacent bins.

17. The method of claim 16, wherein the computing of the frequency spectrum comprises applying a Fast Fourier Transform to the signal representative of the sound.

18. The method of claim 16, further comprising translating the stimulation frequency into a cochlear location.

19. The method of claim 18, further comprising stimulating a pair of electrodes using relative current weights to stimulate a virtual electrode at the cochlear location.

* * * * *